United States Patent [19]

Luotola et al.

[11] Patent Number: 4,731,337
[45] Date of Patent: Mar. 15, 1988

[54] FLUORIMETRIC IMMUNOLOGICAL ASSAY WITH MAGNETIC PARTICLES

[75] Inventors: Juhani E. I. Luotola; Hannu Harjunmaa, both of Espoo, Finland

[73] Assignee: Labsystems Oy, Helsinki, Finland

[21] Appl. No.: 758,539

[22] Filed: Jul. 24, 1985

[30] Foreign Application Priority Data

Jul. 26, 1984 [FI] Finland ................................ 842992

[51] Int. Cl.$^4$ ................ G01N 33/533; G01N 33/538; G01N 33/553
[52] U.S. Cl. .................................... 436/526; 436/533; 436/538; 436/806; 436/824
[58] Field of Search ................ 436/526, 533, 538, 806, 436/824

[56] References Cited

U.S. PATENT DOCUMENTS

| | | | |
|---|---|---|---|
| 4,115,535 | 9/1978 | Glaever | 436/806 X |
| 4,177,253 | 12/1979 | Davies et al. | 436/526 X |
| 4,201,763 | 5/1980 | Monthony et al. | 436/533 X |
| 4,241,176 | 12/1980 | Avrameas et al. | 436/526 X |
| 4,410,660 | 10/1983 | Straus | 436/808 X |
| 4,421,860 | 12/1983 | Elings et al. | 436/533 X |
| 4,576,912 | 3/1986 | Yaverbaum et al. | 436/526 X |

*Primary Examiner*—Sidney Marantz
*Assistant Examiner*—Richard W. Wagner
*Attorney, Agent, or Firm*—Hopgood, Calimafde, Kalil, Blaustein & Judlowe

[57] ABSTRACT

Fluorometric immunological assay method in which an antigen is attached onto magnetic particles, which are, for the time of measurement, pulled against the wall of the measurement vessel by means of the magnetic field. The magnetic particles adhering to the vessel walls are irradiated and the resultant emitted fluorescence is measured.

28 Claims, No Drawings

FLUORIMETRIC IMMUNOLOGICAL ASSAY WITH MAGNETIC PARTICLES

The present invention is concerned with a fluorometric or phosphorometric immunoassay method in which an antibody or antigen marked with a fluorescent or phosphorescent tracer is attached onto small pearls of a solid substance.

In solid phase fluorometric immunoassays (Solid Phase Fluoroimmunoassay) the antigen or antibody is often attached onto small pearls made of polystyrene or polyacrylic. In this way, it is possible to make use of a larger face, to which the antibody or antigen also adheres more readily. The antigen or antibody attached to the solid phase is allowed to react with the antibody or antigen, respectively, present in the sample to be studied and with the antibody or antigen, respectively, marked with a fluorescent molecule. The more there is antibody or antigen in the sample, the less of the marked material adheres to the solid phase. When the antibody or antigen remaining in the liquid phase is separated and the quantity of the marked material adhering to the solid phase is measured by means of a fluorometer, the concentration of the antibody or antigen in the sample is found out.

In the prior-art methods, the extra marked antibody or antigen must be washed off before the fluorometric measurement.

In certain radiological immunoassay methods (RIA), pearls containing a magnetic substance are used which are kept in their position by means of a magnetic field during the removal of liquid or washing.

U.S. Pat. No. 4,438,068 (column 6, lines 8 to 14) proposes also a method in which magnetic particles are used as the solid phase. After the competitive reaction the particles are sedimented by means of a magnet, and the radiation of the labelled particles left in the supernatant is measured through the walls of the test-tube. In the proposed assay the amount of the bound label is measured indirectly from the reaction mixture after sedimenting the smaller portion. Therefore the precision of the assay is not good. The measurement of the liquid phase is more difficult, too. E.g. there may be substances which prevent or cause error in the measurement.

In the solid phase fluoroimmuno assay method in accordance with the present invention, magnetic pearls are used as the solid phase. After the reaction, the magnetic pearls are pulled against the wall of the reaction vessel and the fluorescence (or phosphorescence) radiation is measured through the wall.

The object of the present invention is to provide a fluorometric solid phase immunoassay method in which the extra tracer does not have to be removed out of the measurement vessel containing the pearls before the fluorometric measurement.

In the method in accordance with the present invention, emptying of the measurement vessel and washing of the pearls can be omitted. Thus, all the transfers of liquid related to the assay are additions of liquid. This speeds up the assay and makes its automation decisively easier. The precision of the assay is, however, good, and the liquid phase will not harm the measurement.

According to a preferable embodiment, a colouring agent is added that absorbs strongly at the wavelength of the excitation or emission wavelength. Thus any effect of background radiation from the liquid phase is eliminated.

The method in accordance with the invention is accomplished, for example, as follows:

Antigen of the antibody to be studied is attached to plastic pearls of a size of about 0.2 to 10 $\mu$m, which said pearls contain a magnetic substance. The plastic is, e.g., polystyrene or polyacrylic, and the magnetic substance, e.g., iron, cobalt or nickel.

The pearls are put into a transparent measurement vessel, e.g. a test tube, to which the sample containing the antibody to be studied as well as an antibody marked with a fluorescent molecule are added. Upon completion of the reaction, the quantity of the marked antibody adhering to the antigen on the solid phase is measured in a fluorometer, in which both the excitation radiation is passed into the sample and the fluorescent radiation is collected to the detector through the bottom of the measurement vessel. Moreover, the fluorometer is provided with means for generating a magnetic field, and by its means the pearls are pulled against the bottom of the measurement vessel for the time of the measurement.

Moreover, before the measurement, a colouring agent is added to the sample, either in particle form or in dissolved form. This colouring agent absorbs intensively at the wavelength of the excitation radiation or of the emission radiation. In this way, the quantity of the tracer adhering to the surface of the pearls can be measured accurately without interference by the excess tracer remaining in the liquid phase or by the background radiation with the measurement. The colouring agent is appropriately black, e.g. soot. The colouring agent should, of course, be chosen so that it does not interfere with the reaction of the antigen and antibody or that it does not prevent fluorescence of the tracer.

Of course, the method may also be applied to a method in which phosphorescence is utilized.

What is claimed is:

1. A method of immunological assay for a target antibody or target antigen comprising:
   a. attaching an antigen or antibody to solid magnetic particles;
   b. contacting the magnetic particles resulting from (a) with
      (1) a sample containing either the target antibody or target antigen, and
      (2) fluorescently labeled antibody or fluorescently labeled antigen, respectively, said contacting taking place in a measurement vessel;
   c. forcing the magnetic particles resulting from (b) against the wall of the measuring vessel by an applied magnetic field;
   d. irradiating, through the walls of the measuring vessel, the magnetic particles adhering to the wall as a result of (c); and
   e. measuring the resultant fluorescent or phosphorescent radiation with a detector after this radiation has passed through the walls of the measuring vessel.

2. Method as claimed in claim 1, characterized in that the solid magnetic particles to which the antigen or antibody is attached comprises polymer particles to which a magnetic substance has been added.

3. Method as claimed in claim 1, characterized in that, before measurement, a colouring agent is added in the measurement vessel, said colouring agent having a strong absorption at the wavelength of the exitation radiation.

4. Method as claimed in claim 1, characterized in that, before measurement, a colouring agent is added into the measurement vessel, said colouring agent having a strong absorption at the wavelength of the emission radiation.

5. Method as claimed in claim 3, characterized in that the colouring agent is black.

6. Method as claimed in claim 1, characterized in that both the excitation radiation is passed into the sample and the fluorescence or phosphorescence radiation is collected to the detector through the bottom of the measurement vessel.

7. Method as claimed in claim 2, characterized in that, before measurement, a colouring agent is added into the measurement vessel, said colouring agent having a strong absorption at the wavelength of the excitation radiation.

8. Method as claimed in claim 2, characterized in that, before measurement, a colouring agent is added into the measurement vessel, said colouring agent having a strong absorption at the wavelength of the emission radiation.

9. Method as claimed in claim 3, characterized in that, before measurement, a colouring agent is added into the measurement vessel, said colouring agent having a strong absorption at the wavelength of the emission radiation.

10. Method as claimed in claim 7, characterized in that, before measurement, a colouring agent is added into the measurement vessel, said colouring agent having a strong absorption at the wavelength of the emission radiation.

11. Method as claimed in claim 4, characterized in that the colouring agent is black.

12. Method as claimed in claim 7, characterized in that the colouring agent is black.

13. Method as claimed in claim 8, characterized in that the colouring agent is black.

14. Method as claimed in claim 9, characterized in that the colouring agent is black.

15. Method as claimed in claim 10, characterized in that the colouring agent is black.

16. Method as claimed in claim 2, characterized in that both the excitation radiation is passed into the sample and the fluorescence or phosphorescence radiation is collected to the detector through the bottom of the measurement vessel.

17. Method as claimed in claim 3, characterized in that both the excitation radiation is passed into the sample and the fluorescence or phosphorescence radiation is collected to the detector through the bottom of the measurement vessel.

18. Method as claimed in claim 4, characterized in that both the excitation radiation is passed into the sample and the fluorescence or phosphorescence radiation is collected to the detector through the bottom of the measurement vessel.

19. Method as claimed in claim 5, characterized in that both the excitation radiation is passed into the sample and the fluorescence or phosphorescence radiation is collected to the detector through the bottom of the measurement vessel.

20. Method as claimed in claim 7, characterized in that both the excitation radiation is passed into the sample and the fluorescence or phosphorescence radiation is collected to the detector through the bottom of the measurement vessel.

21. Method as claimed in claim 8, characterized in that both the excitation radiation is passed into the sample and the fluorescence or phosphorescence radiation is collected to the detector through the bottom of the measurement vessel.

22. Method as claimed in claim 9, characterized in that both the excitation radiation is passed into the sample and the fluorescence or phosphorescence radiation is collected to the detector through the bottom of the measurement vessel.

23. Method as claimed in claim 10, characterized in that both the excitation radiation is passed into the sample and the fluorescence or phosphorescence radiation is collected to the detector through the bottom of the measurement vessel.

24. Method as claimed in claim 11, characterized in that both the excitation radiation is passed into the sample and the fluorescence or phosphorescence radiation is collected to the detector through the bottom of the measurement vessel.

25. Method as claimed in claim 12, characterized in that both the excitation radiation is passed into the sample and the fluorescence or phosphorescence radiation is collected to the detector through the bottom of the measurement vessel.

26. Method as claimed in claim 13, characterized in that both the excitation radiation is passed into the sample and the fluorescence or phosphorescence radiation is collected to the detector through the bottom of the measurement vessel.

27. Method as claimed in claim 14, characterized in that both the excitation radiation is passed into the sample and the fluorescence or phosphorescence radiation is collected to the detector through the bottom of the measurement vessel.

28. Method as claimed in claim 15, characterized in that both the excitation radiation is passed into the sample and the fluorescence or phosphorescence radiation is collected to the detector through the bottom of the measurement vessel.

* * * * *